(12) United States Patent
Masui et al.

(10) Patent No.: US 7,308,951 B2
(45) Date of Patent: Dec. 18, 2007

(54) METHOD OF CORING A CRUSTAL CORE SAMPLE AND FLOW-ABLE COATING MATERIAL FOR CORING A CRUSTAL CORE SAMPLE

(75) Inventors: Noriaki Masui, Kanagawa (JP); Shigeru Deguchi, Kanagawa (JP); Kaoru Tsujii, Kanagawa (JP)

(73) Assignee: Independent Administrative Institution, Japan Agency for Marine-Earth Science and Technology, Yokosuka-shi, Kanagawa (JP)

( * ) Notice: Subject to any disclaimer, the term of this patent is extended or adjusted under 35 U.S.C. 154(b) by 296 days.

(21) Appl. No.: 11/063,926

(22) Filed: Feb. 22, 2005

(65) Prior Publication Data

US 2005/0183886 A1    Aug. 25, 2005

(30) Foreign Application Priority Data

Feb. 24, 2004    (JP) ............................ 2004-048144

(51) Int. Cl.
*E21B 25/08*    (2006.01)
(52) U.S. Cl. ..................................... 175/58
(58) Field of Classification Search .............. 175/20, 175/58, 226, 233, 249
See application file for complete search history.

(56) References Cited

U.S. PATENT DOCUMENTS

| 5,482,123 A | * | 1/1996 | Collee ......................... 175/58 |
| 5,881,825 A | * | 3/1999 | Collee et al. ................. 175/58 |
| 6,695,076 B2 | | 2/2004 | Masui et al. |

FOREIGN PATENT DOCUMENTS

JP    2002-228558 A    8/2002

OTHER PUBLICATIONS

Thomas W. Beihoffer et al., "Cationic polymer drilling fluid can sometimes replace oil-based mud," *Oil & Gas Journal*, Mar. 16, 1992, pp. 47-52.

* cited by examiner

*Primary Examiner*—Lanna Mai
*Assistant Examiner*—Matthew J. Smith
(74) *Attorney, Agent, or Firm*—Frishauf, Holtz, Goodman & Chick, P.C.

(57)    ABSTRACT

Disclosed herein is a method of coring a crustal core sample, which comprises using a crustal core sampler equipped with a flow-able coating material-ejecting mechanism for ejecting a flow-able coating material, and ejecting the flow-able coating material composed of a polymer substance having a colloidal particles capturing ability by aggregating function and a water-absorbing polymer substance, from the flow-able coating material-ejecting mechanism of the crustal core sampler thereby coring a crustal core sample in a state coated with the flow-able coating material.

6 Claims, 11 Drawing Sheets

METHOD OF CORING A CRUSTAL CORE SAMPLE AND FLOW-ABLE COATING MATERIAL FOR CORING A CRUSTAL CORE SAMPLE

BACKGROUND OF THE INVENTION

1. Field of the Invention

The present invention relates to a method of coring a crustal core samples used for various researches, for example, biological researches on subsurface microorganisms or the like in a crustal core, and chemical, physical and geological researches, and a flow-able coating material for coring a crustal core sample.

2. Description of the Background Art

In recent years, researches on crustal interiors have been advanced, and the presence of the subsurface microorganisms under a deep-depth, high-temperature and high-pressure environment in a crustal interior has been reported. According to researches on the subsurface microorganisms in a deep sphere composed of these subsurface microorganisms, there is a possibility that important findings, for example, elucidation of influences by material conversion and mass transfer in a deep geological environment, elucidation of origin of life in the primitive earth and evolution thereof, or development of drugs and novel materials may be obtained. Further, chemical researches, physical researches or geological researches in such a deep-depth crustal interior are advanced from various points of view.

A crustal core sample used for such various researches as described above can be taken with comparative ease from the crust at the depth closer to mantle by drilling a submarine crust by means of, for example, a drill ship.

As an example of a method of conducting the drilling using the drill ship, for example, a riser drilling method has been generally known. In this method, a drill pipe extending from the drill ship to the sea bottom is rotated to drill the crust by means of a drill bit provided on the tip thereof and at the same time, a fluid (hereinafter also referred to as "working fluid") for drilling work, such as so-called drilling mud or sea water, the specific gravity, viscosity, chemical composition, etc. of which have been adjusted according to the condition of the crust drilled, is fed to the drill bit to remove drill debris, and to protect and stabilize a side wall of the drill hole. Since the working fluid is fed through a circulating channel in the riser drilling method, the fluid is also referred to as "circulating fluid".

A crustal core sample taken by such a method has a great possibility that the state of the sample present in the crust as it is may be lost by an influence exerted from the outside during the coring operation, for example, by contact of the working fluid containing drill debris. In such a case, there is a possibility that the crustal core sample cored may become a sample lost its important information for intended researches.

In order to overcome with such a problem, there is disclosed a method of coring a crustal core sample, that an outer surface of the crustal core sample is coated with a flow-able coating material composed of gel or the like when the crustal core sample is taken, thereby obtaining the crustal core sample in a state that its mechanical structure or tissue has been protected from the outside (see, for example, U.S. Pat. No. 5,482,123).

As described below, it is also known to use an antimicrobial substance as a flow-able coating material, thereby taking a crustal core sample in a state protected from contamination with, for example, adventitious nonindigeneous microorganisms (see, Japanese Patent Application Laid-Open No. 2002-228558).

FIG. 1 illustrates a case where a sea bed crust is drilled by means of a drill ship in accordance with the riser drilling method.

In this drilling method, a drilling operation is conducted by a riser drilling system provided on a drill ship 10 on the surface 13 of the sea. In the riser drilling system, a riser pipe 20 extending downward from the drill ship 10 into the sea to connect between the drill ship 10 and a sea floor 15 is provided, and a drill pipe 21 is arranged within this riser pipe 20. This drill pipe 21 is so constructed that its upper end is connected to a power swivel 11 that is a rotating drive mechanism on the drill ship 10, and its lower part enters the crust 16 through a blowout-preventing device 14. A drill bit 30 is provided at the lower end of the drill pipe 21.

The drill ship 10 is generally equipped with an automatic ship position keeping system constructed by correlating a plurality of thrusters 12a, 12b and 12c provided on the bottom of the ship, a differential global positioning system (DGPS) making good use of, for example, an artificial satellite, and the like. According to this automatic ship position keeping system, the position of the ship can be held within a region of a small radius centering an intended drill hole in the sea floor 15 without being affected by the wind, the tidal current and the like even in the open sea.

The drill bit 30 is so constructed that a plurality of semispherical cutter parts each protruding downward are formed at a lower end of an outer barrel 23 (see FIG. 11) so as to stand in its peripheral direction, and a plurality of cutter elements 31 (see FIG. 11) are fixed to each of the cutter parts.

The drill bit 30 is rotated through the drill pipe 21 by the power swivel 11, whereby the crust 16 is drilled from the sea floor 15, and the lower end of the drill pipe 21 goes down in the crust 16. At this time, a working fluid composed of drilling mud, seawater or the like is fed to the drill bit 30 through the drill pipe 21 in the riser pipe 20. A plurality of casing pipes 17 different in length from each other provided at the lower part of the blowout-preventing device 14 are inserted according to the depth of the drilling, whereby collapse of the wall surface in the drill hole is prevented.

Numbers of safety valves for pressure relief are provided in the blowout-preventing device 14, and the pressure within the drill hole is controlled by these safety valves, whereby rapid blowout of high-pressure hydrocarbon gases, interstitial water within the crust and/or the like is controlled to surely continue a safe drilling process.

FIG. 2 is a partial sectional view illustrating details of compositional units making up a riser pipe together with a section of a main pipe, taken along its axis, in a state that a drill pipe has been inserted therein.

As illustrated in FIG. 2, the riser pipe 20 is constructed by the main pipe 22 and a kill & choke line 27 provided independently of the main pipe 22, and a double-piped structure is formed by the main pipe 22 and the drill pipe 21 arranged in the main pipe 22. A circulating fluid-running channel 24, through which the working fluid is fed, is formed by an internal space of the drill pipe 21. Through this internal space, various devices, for example, a mechanism forming a crustal core sampler, and the like, are guided to the drill hole. On the other hand, a circulating channel, through which the working fluid is returned back to the drill ship 10, is defined by an annular channel 25 formed between an inner peripheral wall surface of the main pipe 22 and an outer peripheral surface of the drill pipe 21.

More specifically, the working fluid is fed to the drill bit 30, ejected within the drill hole from working fluid-ejecting openings provided at lower end of the drill bit 30 and then circulated through the annular channel 25. This working fluid is a fluid the specific gravity, viscosity, chemical composition and the like of which have been adjusted according to, for example, the geology of the crust. For example, that obtained by mixing various modifiers into muddy water available in a drilling site may be used.

Incidentally, the necessary lengths of the main pipe 22 and the drill pipe 21, and increases thereof are actually achieved by successively joining a great number of respective elements thereof to one another as needed. In FIG. 2, reference numeral 28 indicates a line holder.

The above-described riser drilling method has such merits as described below, whereby a drilling work can be stably conducted.

(1) Removal of Drill Debris:

Drill debris collected on the bottom of the drill hole is conveyed to the drill ship 10 through the annular channel 25 by the working fluid ejected from the drill bit 30.

(2) Protection and Stabilization of Wall Surface of Drill Hole:

The viscous component in the working fluid ejected from the drill bit 30 adheres to the wall surface of the drill hole to form a thin protective film 18 (cf. FIG. 5), whereby collapse of the wall surface in the drill hole is prevented.

The specific gravity in the composition of the working fluid is adjusted, whereby the equilibration of pressure against the formation pressure in a deep depth can be conducted, and an effect of preventing a fluid in the formation from penetrating into the drill hole is brought about.

(3) Cooling and Lubrication of Drill Bit:

The drill bit 30 is cooled by contacting of the working fluid with its surface to prevent it from being excessively heated by gradually rising crustal heat, and lubricating effect is achieved between the drill bit 30 and the crust, so that the degree of friction in the drill bit 30 is lowered to lessen the abrasion of the drill bit 30. (4) The constitutive substances and the like of the drill debris contained in the working fluid sent on to the drill ship 10 are successively analyzed and monitored, whereby the geological condition of the crust, to which drilling is being conducted at this very moment, is easy to be always confirmed and grasped.

As understood from the above fact, the drill pipe 21 and drill bit 30 for drilling the crust 16 are required to permit feeding and ejecting the working fluid from the tip parts thereof, and the so-called coring drill bit having an opening at a central part along a rotating axis thereof is preferably used.

A case where a crustal core sample is cored by the riser drilling method using a conventional crustal core sampler disclosed in U.S. Pat. No. 5,482,123 is then specifically described.

FIGS. 11 and 12 are sectional views illustrating the states, in terms of sections, of a drill pipe and a drill bit in a drilling work. FIG. 11 illustrates a state right after drilling is started, while FIG. 12 illustrates a state that the drilling has been advanced.

In the crustal core sampler in this example, a pipe-like inner barrel 60 is arranged, in a mode that a thrust bearing (not illustrated) is intervened, in an outer barrel 23 making up a drill pipe 21 and provided with a drill bit 30 at the tip thereof.

At a lower end of the inner barrel 60, a disk-like flow-able coating material-ejecting opening member 62 is arranged in a state that liquid-tightness is retained so as to close the opening of the inner barrel through a ring-like sealing member 61, and relatively movably in a vertical direction within the inner barrel 60.

In this flow-able coating material-ejecting opening member 62, is formed flow-able coating material-ejecting holes 68 linking the interior of the inner barrel 60 with the outside and extending through in a vertical direction and is provided an opening and closing valve 65 for opening and closing the flow-able coating material-ejecting holes 68. In other words, the opening and closing valve 65 is constructed by a valve body member 64 arranged vertically movably on the inner side (upper surface side) of the flow-able coating material-ejecting opening member 62, a connecting rod 63 extending slidably in a vertical direction through the flow-able coating material-ejecting opening member 62 and a working disk 66 provided at a lower end of the connecting rod 63 and located on the outer side (lower surface side) of the flow-able coating material-ejecting opening member 62. The connecting rod 63 has a length longer than the thickness in the vertical direction of the flow-able coating material-ejecting opening member 62. A flow-able coating material 67 is filled in the interior of the inner barrel 60.

In the riser drilling method using the crustal core sampler having the structure described above, as illustrated in FIG. 11, the outer barrel 23 in a state rotated about an axis of the barrel, and the inner barrel 60 retained in a standstill state in this rotational direction by the thrust bearing which is not illustrated go down from the sea floor 15 when drilling of the crust 16 is started, whereby the working disk 66 provided at the lower end in the connecting rod 63 is pushed up relatively upward by the sea floor 15, and the valve body member 64 is separated from the inner surface (upper surface) of the flow-able coating material-ejecting opening member 62 through the connecting rod 63 to open the flow-able coating material-ejecting holes 68. As a result, a state that the interior of the inner barrel 60 is linked with the outside is created, and the flow-able coating material 67 in the inner barrel 60 is ejected to the outside through the flow-able coating material-ejecting holes 68.

As illustrated in FIG. 12, a columnar crustal core portion P formed by drilling the periphery thereof with the downward movement of the outer barrel 23 and inner barrel 60 by the progress of the drilling, enters the interior of the inner barrel 60 from the central opening of the drill bit 30 while forming a narrow annular gap G between the outer peripheral surface of the columnar crustal core portion P and the inner peripheral wall surface of the inner barrel 60, and moreover the flow-able coating material-ejecting opening member 62 is moved relatively upward within the inner barrel 60 together with the columnar crustal core portion P gradually grown while retaining the state that the flow-able coating material-ejecting holes 68 has been linked with the interior.

As a result, the flow-able coating material 67 is ejected into the annular gap G through the flow-able coating material-ejecting holes 68 and adheres to the outer peripheral surface of the columnar crustal core portion P gradually grown.

The columnar crustal core portion P entered into the inner barrel 60 is broken at a lower portion thereof and taken. This crustal core portion is recovered as a crustal core sample with the inner barrel 60 on the drill ship 10 through the interior of the drill pipe 21 by a wire or the like.

However, it becomes clear that it is not possible to sufficiently and surely prevent the obtained crustal core sample from being contaminated by adventitious microorganism even in the case where the flow-able coating material is used in a method of coring a crustal core sample utilizing the working fluid such as mud water. This is because that although a coating material layer is formed on the outer surface of the cored crustal core sample, the contaminants originated from working fluid are adhered onto the surface of the crustal core sample, since the working fluid is contacted to the surface before the coating material is adhered. In other words, it is thought that it is because, since the working fluid is that composed of a large quantity of microscopic particles having the particle diameter of, for example, at most 1 µm contained in water as colloidal particles, contaminants such as adventitious microorganism and the like are adhered on to the outer surface of the crustal core sample being formed, by being mediated by the water and the microscopic particles of the working fluid, and furthermore, the contaminants enter into the inside of the surface layer.

Especially, when the crustal substance which is an object of drilling is comparatively soft rock, the columnar crustal core portion obtained becomes small in diameter because of the vibration of the drill bit in a radial direction during the drilling. As a result, the annular gap G in the inner barrel becomes larger and it allows a large quantity of working fluid to enter into the annular gap G, thereby a possibility of adhesion of the contaminants to the crustal core sample to be obtained becomes high.

SUMMARY OF THE INVENTION

The present invention has been made on the basis of the foregoing circumstances and has as its object the provision of a method of coring a crustal core sample, by which a crustal core sample can be cored in a state sufficiently and surely prevented from any contamination.

Another object of the present invention is to provide a flow-able coating material for coring a crustal core sample, by which a crustal core sample can be coated in a state sufficiently and surely prevented from any contamination by its specific property.

According to the present invention, there is thus provided a method of coring a crustal core sample, which comprises using a crustal core sampler equipped with a flow-able coating material-ejecting mechanism for ejecting a flow-able coating material, and ejecting the flow-able coating material formed of a polymer substance having a colloidal particles capturing ability by aggregating function, and a water-absorbing polymer substance from the flow-able coating material-ejecting mechanism of the crustal core sampler, thereby coring a crustal core sample in a state coated with the flow-able coating material.

In the above-described method, can be used the crustal core sampler equipped with a drilling mechanism for drilling the crust so as to form an annular drilled groove, a supplying mechanism of a fluid for drilling work having an ejection opening of the fluid for drilling work positioned at the lower end of the drilling mechanism, and a cylindrical barrel, which has an opening for inserting a columnar crustal core portion at its lower end and receives a columnar crustal core portion provided as a crustal core sample in the interior thereof, and wherein the barrel is equipped with the flow-able coating material-ejecting mechanism for ejecting the flow-able coating material inwardly in a radial direction of the barrel at a position in close vicinity of its lower end.

Further, the crustal core sampler may comprise a cylindrical drill pipe equipped at its lower end with a drill bit having an ejection opening of a fluid for drilling work, and an inner barrel arranged in the drill pipe, and wherein the inner barrel may be equipped with a cylindrical inner barrel body, which has an opening for inserting a columnar crustal core portion at its lower end and receives a columnar crustal core portion formed by drilling and provided as a crustal core sample in the internal space thereof, a core elevator arranged in an internal space of the inner barrel body and movably in an axial direction thereof, and the flow-able coating material-ejecting mechanism which comprises a channel-forming member for forming a flow-able coating material-running channel with an outer peripheral surface of the inner barrel body and flow-able coating material-ejecting openings for ejecting the flow-able coating material from the flow-able coating material-running channel inwardly in a radial direction of the inner barrel body at a position in close vicinity of the lower end of the inner barrel body, and the inner barrel may be arranged in such a manner that the opening for inserting the columnar crustal core portion is positioned above the ejection opening of the fluid for drilling work in the drill pipe.

In the above-described method, the polymer substance having a colloidal particles capturing ability by aggregating function can be selected from cationic polymer substance, anionic polymer substance and nonionic polymer substance.

Further, at least either one of the polymer substance having a colloidal particles capturing ability by aggregating function or the water-absorbing polymer substance may preferably have an antimicrobial property.

According to the present invention, there is also provided a flow-able coating material for coring a crustal core sample which comprises polymer substance having a colloidal particles capturing ability by aggregating function and water-absorbing polymer substance, which is used to coat a crustal core sample in a coring of the crustal core sample by drilling the crust.

According to the method of coring a crustal core sample of the present invention, the outer surface of the crustal core sample cored by the crustal core sampler is coated with a coating material ejected from the crustal core sampler, and the coating material according to the present invention is composed of a polymer substance (hereinafter also referred to as "colloidal particles capturing polymer substance") having a colloidal particles capturing ability by aggregating function and a water-absorbing polymer substance. Therefore, the colloidal particles in the working fluid and adhered on to the outer surface of the crustal core sample by a contact of the working fluid in advance to the coating material, are captured by aggregation function of the colloidal particles capturing polymer substance in the coating material layer which is in contact with the colloidal particles, and at the same time, water in the working fluid adhered on to the outer surface of the crustal core sample, is absorbed by the water-absorbing polymer substance which is in contact therewith and fixed. As a result, contaminants from working fluid, namely, microorganism and other contaminants introduced on to the outer surface of the crustal core sample along with the colloidal particles and the water contained in the working fluid, are fixed in the coating material layer, and a transfer of the contaminants to the crustal core sample is inhibited, thereby the crustal core sample can be cored in a state sufficiently and surely prevented from contamination by the contaminants.

In the above-described method, as the polymer substance having a colloidal particles capturing ability by aggregating function, the polymer substance which exhibit an expected colloidal particles capturing ability by aggregating function, is selected from cationic polymer substance, an ionic polymer substance and nonionic polymer substance according to the properties of the working fluid actually used, more specifically, according to a kind of microscopic particles contained in the working fluid, and used, thereby the above-describing functional effects can be obtained with certainty.

Further, in case when at least one of the colloidal particles capturing polymer substance or the water-absorbing polymer substance has an antimicrobial property, activities and increase of microorganisms adhered in advance can be controlled or prevented, and at the time, enter of microorganisms from the exterior is prevented, thereby contamination of crustal core sample being caused by these factors can be prevented.

According to the flow-able coating material for a coring a crustal core sample of the present invention, there can be obtained the above-described functional effects by being used in the method of coring a crustal core sample.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE PREFERRED EMBODIMENTS

The crustal core samplers used in the method of coring a crustal core sample according to the present invention will hereinafter be described in detail. The crustal core samplers are particularly suitably used in, for example, the riser drilling method carried out in the above-described mode.

Figure 3:
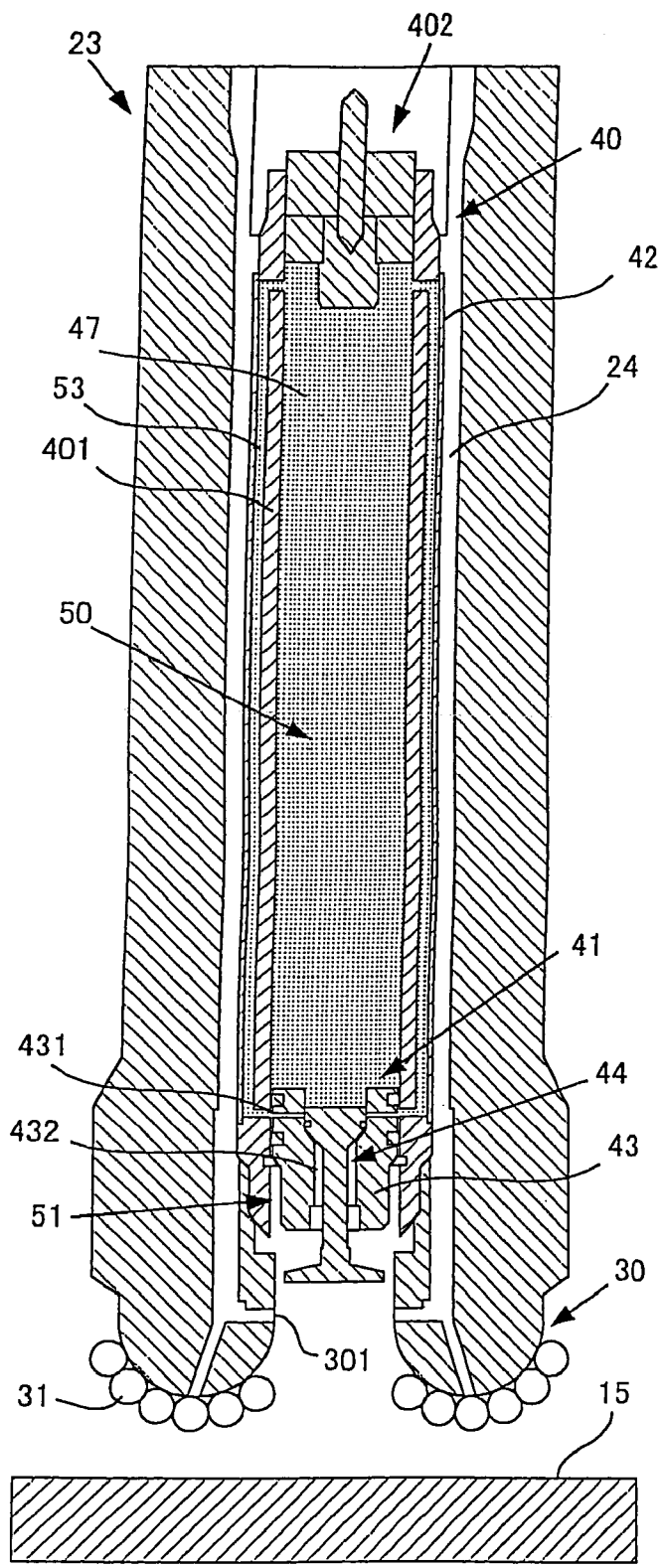
FIG. 3 is a sectional view illustrating a drill pipe and a drill bit right before submarine drilling is started, with a section taken along an axis of the pipe partly schematically shown.
Figure 4:
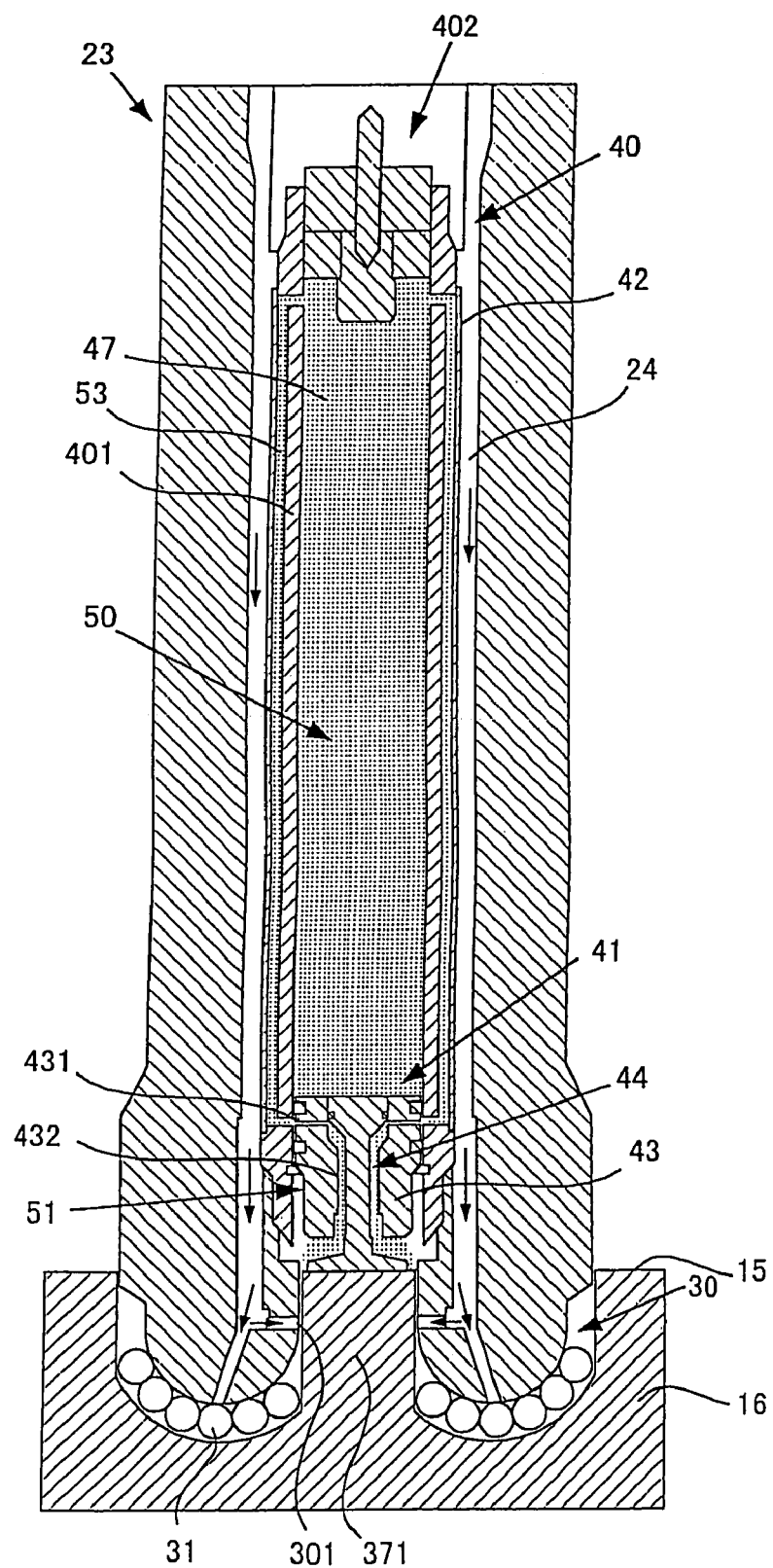
FIG. 4 is a sectional view illustrating the drill pipe and the drill bit right after the submarine drilling is started, with a section taken along the axis of the pipe partly schematically shown.
Figure 5:
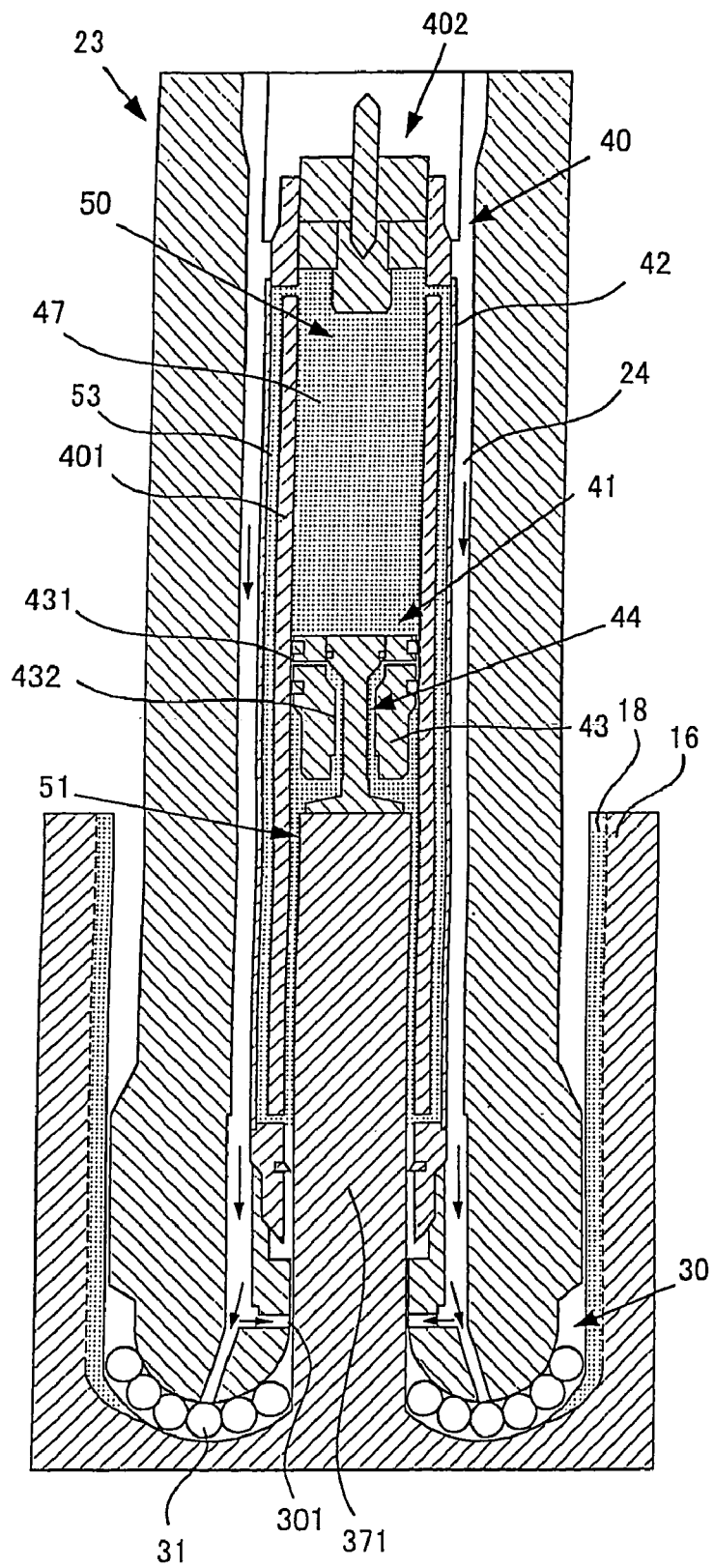
FIG. 5 is a sectional view illustrating the drill pipe and the drill bit during the submarine drilling, with a section taken along the axis of the pipe partly schematically shown.
Figure 6:
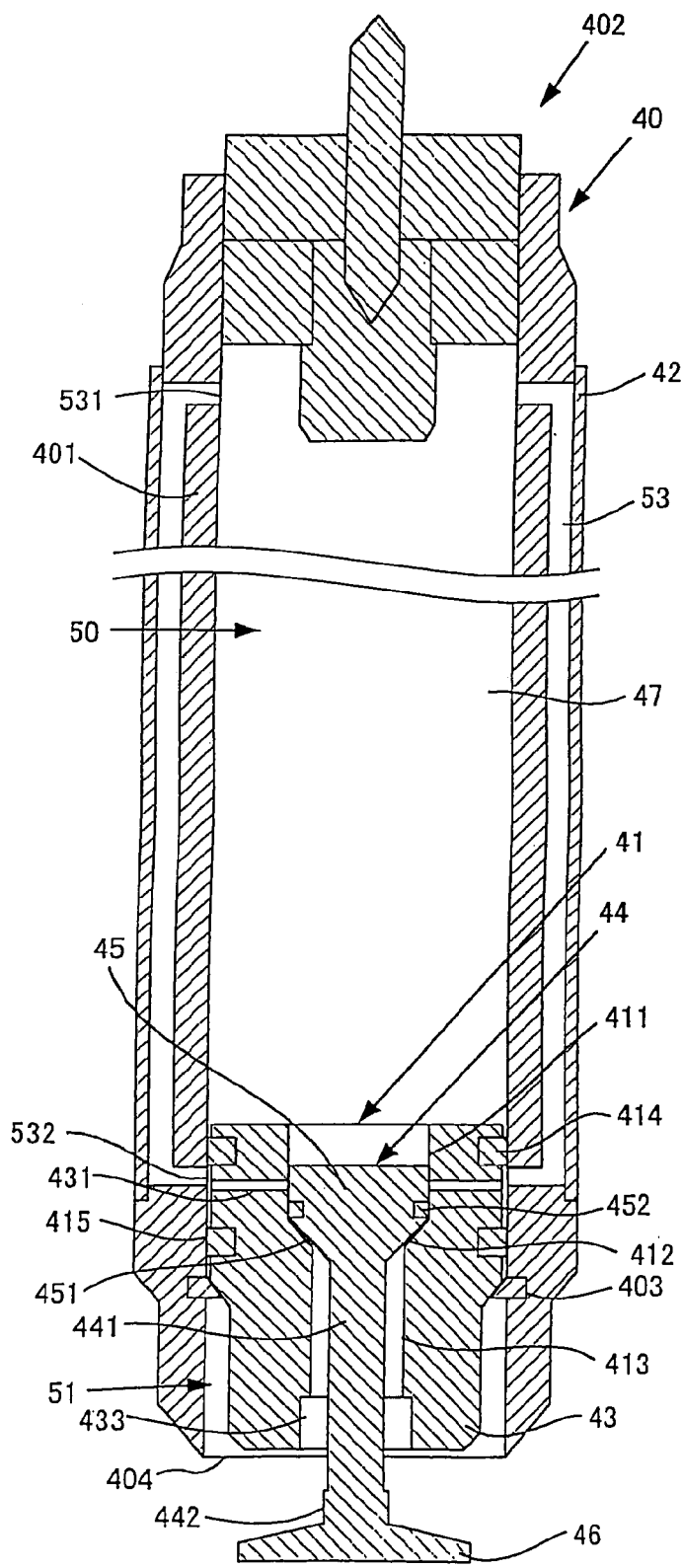
FIG. 6 is a sectional view illustrating, on an enlarged scale, the construction of a crustal core sampler according to the present invention.
Figure 7:
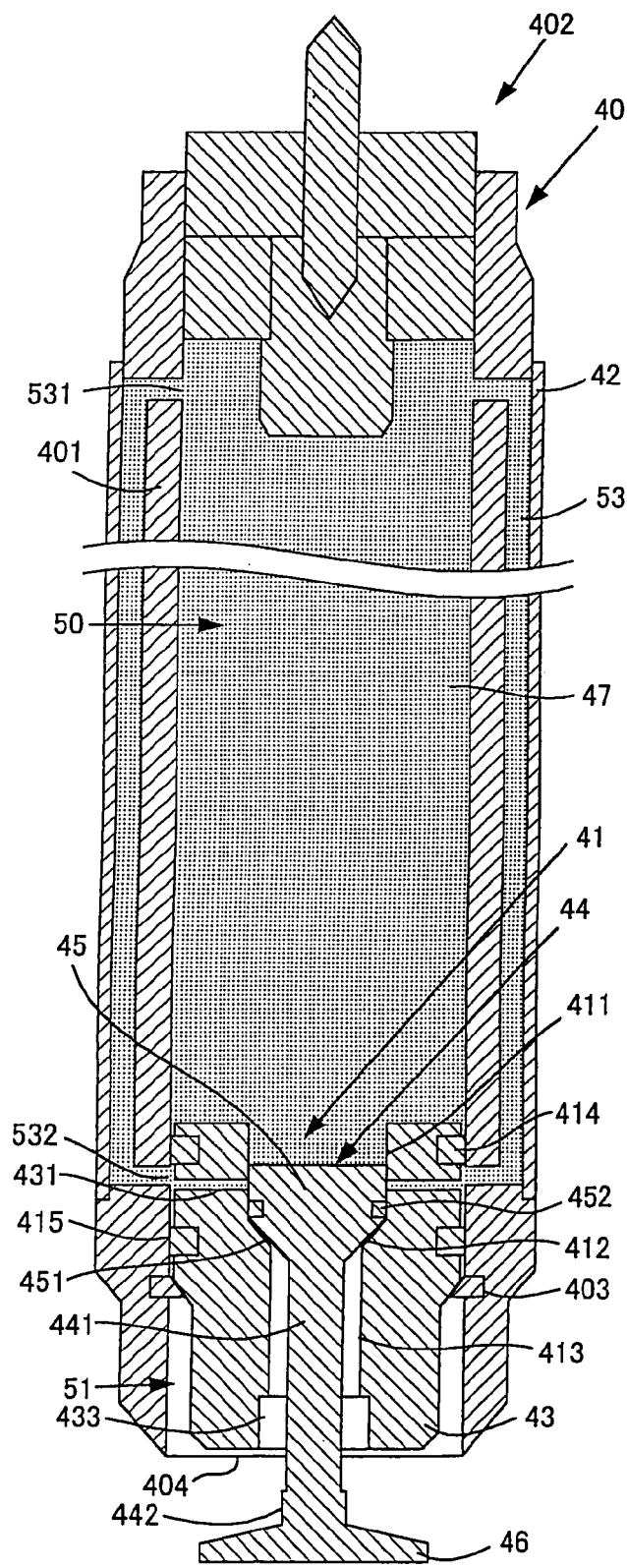
FIG. 7 is a sectional view illustrating, on an enlarged scale, the crustal core sampler in the operation state shown in FIG. 3.
Figure 8:
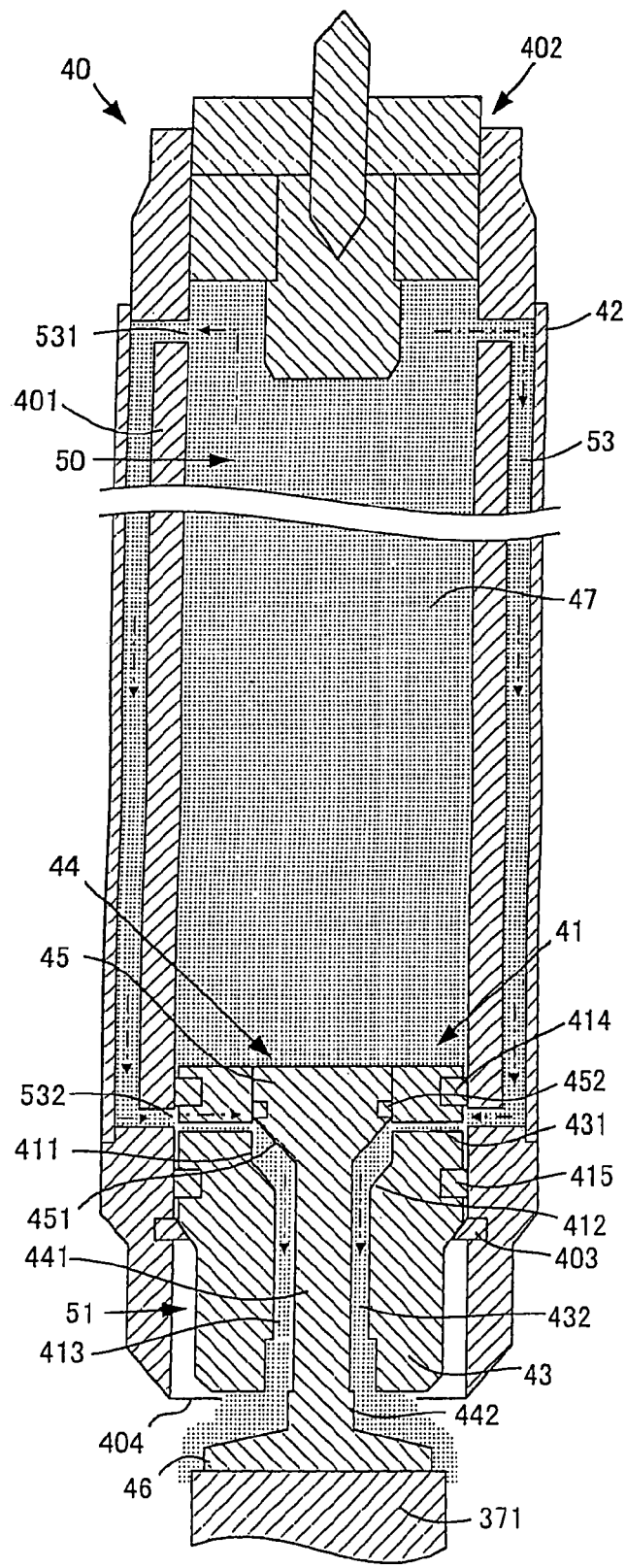
FIG. 8 is a sectional view illustrating, on an enlarged scale, the crustal core sampler in the operation state shown in FIG. 4.
Figure 9:
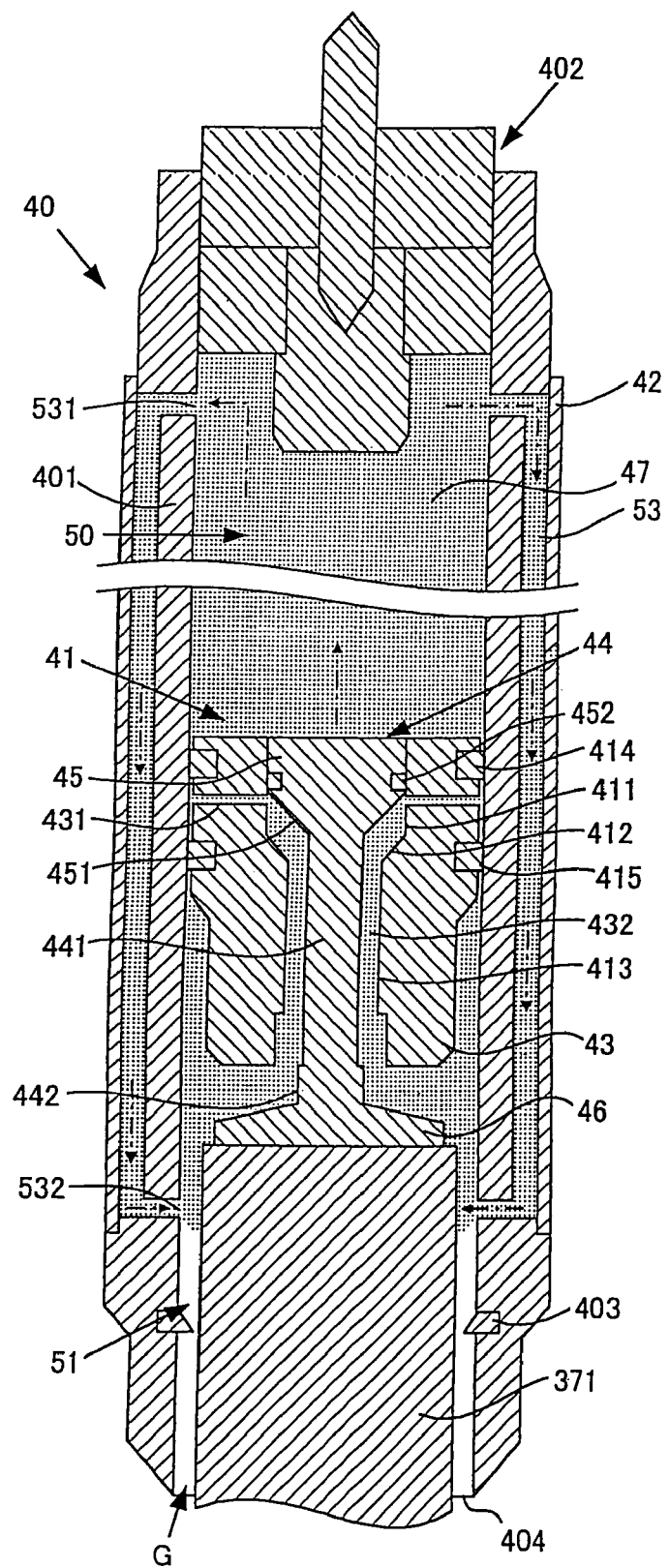
FIG. 9 is a sectional view illustrating, on an enlarged scale, the crustal core sampler in the operation state shown in FIG. 5.

FIGS. 3 to 5 are sectional views illustrating the states of an outer barrel, in which a crustal core sampler has been arranged, and a drill bit in drilling operation, with a section taken along the axis of the barrel. FIG. 3 illustrates a state right before drilling of the crust is started, FIG. 4 a state right after the drilling of the crust is started, and FIG. 5 a state that the drilling of the crust has been advanced to some extent. FIG. 6 is a sectional view illustrating, on an enlarged scale, the construction of the crustal core sampler. FIGS. 7 to 9 are sectional views illustrating, on an enlarged scale, the crustal core sampler in various operation states respectively shown in FIGS. 3 to 5.

Figure 1:
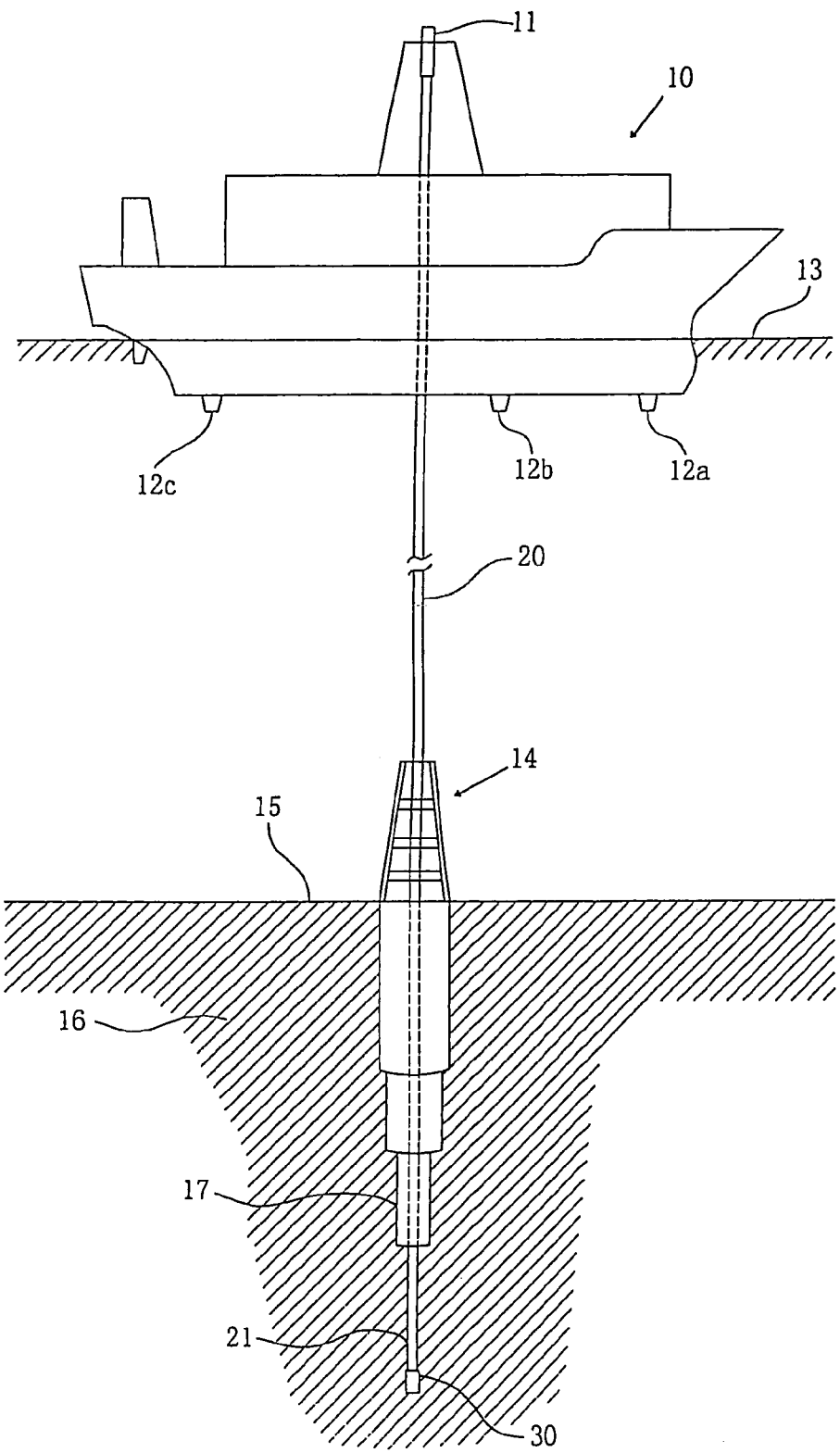
FIG. 1 illustrates a case where a submarine crust is drilled by means of a drill ship in accordance with the riser drilling method.
Figure 2:
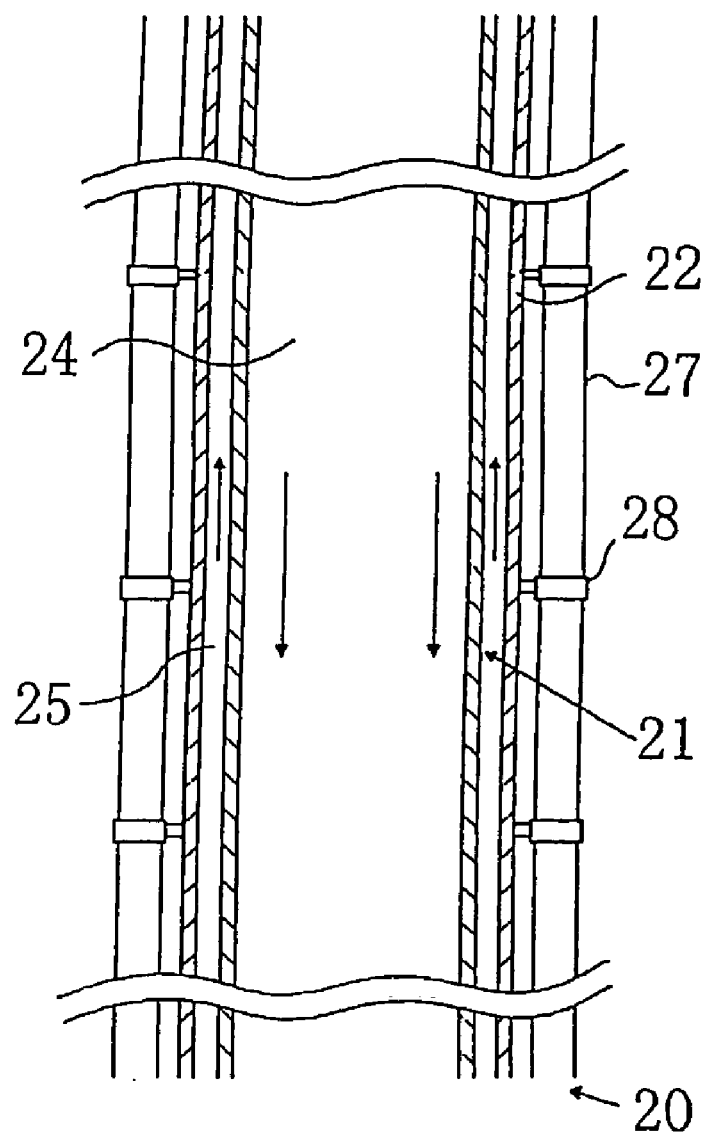
FIG. 2 is a partial sectional view illustrating details of compositional units making up a riser pipe together with a section of a main pipe, taken along its axis, in a state that a drill pipe has been inserted therein.

The crustal core sampler comprises a cylindrical outer barrel 23 making up a drill pipe 21 (see FIGS. 1 and 2) and equipped with a drill bit 30 at its lower end, and an inner barrel 40 arranged within the outer barrel 23. The drill bit 30 is provided with working fluid-ejecting openings 301 at its lower end.

The inner barrel 40 is equipped with a cylindrical inner barrel body 401, the upper end opening of which is closed with a closing member 402, and which has an opening 404 (see FIG. 6) for inserting a columnar crustal core portion at its lower end, a core elevator 41 arranged in an internal space of the inner barrel body 401 and movably in an axial direction thereof, a cylindrical channel-forming member 42 integrally provided with the inner barrel body 401 for forming a cylindrical flow-able coating material-running channel 53 with an outer peripheral surface of the inner barrel body 401, and flow-able coating material-ejecting openings 532 (see FIG. 6) for ejecting a flow-able coating material 47 inwardly in a radial direction of the inner barrel body 401 at a position in close vicinity of the opening 404 for inserting the columnar crustal core portion in the inner barrel body 401.

As illustrated in FIG. 3, the inner barrel 40 is arranged in such a manner that the opening 404 for inserting the columnar crustal core portion in the inner barrel body 401 is positioned above the working fluid-ejecting openings 301 of the drill bit 30.

In the inner barrel 40, a flow-able coating material-ejecting mechanism for ejecting the flow-able coating material is formed by the flow-able coating material-running channel 53 and the flow-able coating material-ejecting openings 532.

In FIGS. 6 and 7, the core elevator 41 is illustrated in a state positioned at the lowest position that movement to a position lower than this is restricted in the internal space of the inner barrel body 401 by being supported by a stopper 403 formed projectingly inwardly from an inner peripheral wall surface of the inner barrel body 401. In the state that the core elevator 41 has been positioned at the lowest position as described above, a region partitioned by 2 O-rings 414 and 415 in an outer peripheral surface of a core elevator body 43, which will be described subsequently, faces the flow-able coating material-ejecting openings 532 to achieve a state that linking holes 431 have been linked with the flow-able coating material-ejecting openings 532.

In this embodiment, the inner barrel 40 is so constructed that its inner diameter is somewhat greater than a diameter of the innermost peripheral surface of loci drawn by rotation of cutter elements 31 of the drill bit 30, i.e., an outer diameter of a columnar crustal core portion 371 formed by drilling as described below.

As illustrated in FIG. 6, the flow-able coating material-running channel 53 is linked with a plurality of inlet openings 531 radially extending so as to open into the internal space of the inner barrel body 401 at its upper end, and also linked with a plurality of the flow-able coating material-ejecting openings 532 radially extending so as to open into the internal space of the inner barrel body 401 at its lower end.

The core elevator 41 is composed of a cylindrical core elevator body 43 having a central through-hole and arranged in a state that its outer peripheral surface liquid-tightly and slidably comes into contact with an inner peripheral surface of the inner barrel body 401 over the whole periphery though the 2 O-rings 414 and 415 arranged in a state separated from each other in a vertical direction. In the core elevator body 43, the linking holes 431 for linking the space in the central through-hole with the flow-able coating material-ejecting openings 532 are formed in a region between the 2 O-rings 414 and 415, and an opening and closing valve body 44 for controlling a linked state between the space in the central through-hole and the linking holes 431 by moving in a vertical direction in the central through-hole is arranged.

Specifically, the central through-hole in the core elevator body 43 is defined by vertically linking an upper space part 411 opening into an upper side with a lower space part 413 having an inner diameter smaller than the upper space part 411 and opening into a lower side through a tapered part 412 whose inner diameter becomes smaller toward the lower side.

The linking holes 431 are so formed that their one ends open into an outer peripheral surface of the core elevator body 43 in a region partitioned by the upper O-ring 414 and the lower O-ring 415 and extend inwardly in a radial direction, and the other ends open into a lower portion of the upper space part 411 to form a valve opening.

On an inner peripheral surface of the lower space part 413 in the core elevator body 43, a plurality of projected contact parts 433 each projecting inwardly in a radial direction are provided in a state separated from each other in a peripheral direction so as to come into contact with a flange 442 of a rod part 441, which will be described subsequently, at its lower end position.

The opening and closing valve body 44 has a columnar valve body part 45 whose outer diameter conforms to an inner diameter of the upper space part 411 and whose thickness in a vertical direction is smaller than the height of the upper space part 411, a tapered connecting part 451 integrally formed with the valve body part 45 at a lower end of the valve body part, whose outer diameter becomes smaller toward the lower side, a columnar rod part 441 extending from a lower end of the connecting part 451 to a lower side and having an outer diameter smaller than an inner diameter of the lower space part 413, and a working disk 46 integrally formed with the rod part 441 at a lower end of the rod part and having an outer diameter greater than the outer diameter of the valve body part 45 and smaller than the inner diameter of the inner barrel body 401. The flange 442 projecting outward in the radial direction over the whole periphery is provided at a lower end portion of the rod part 441.

In the outer peripheral surface of the columnar valve body part 45, an O-ring 452 liquid-tightly sliding on the inner peripheral surface of the upper space part 411 is provided at its lower end.

When the opening and closing valve body 44 in the core elevator 41 is relatively moved upward as illustrated in FIG. 8, the connecting part 451 is separated upward from the tapered part 412, whereby a substantially cylindrical linking channel 432 opening into a lower side is formed between the core elevator body 43 and the opening and closing valve body 44.

In the inner barrel 40 having the above-described structure, a flow-able coating material reservoir 50 for holding the flow-able coating material 47 is partitioned above the core elevator 41 by the internal space of the inner barrel body 40. When the core elevator 41 is relatively lifted, however, the volume of the flow-able coating material reservoir 50 is gradually reduced, and at the same time a crustal core sample-receiving space 51 (see FIG. 9) for receiving a columnar crustal core portion 371 formed by drilling is gradually formed.

Such a crustal core sampler as described above can be specifically constructed and used as a part of, for example, a standard rotary core barrel (RCB), piston type core barrel (advanced piston corer APC), motor-driven core barrel (MDCB), pressure-retaining core barrel (PCS) or the like. These are used properly according the geological condition of the crust.

The crustal core sampler having such construction as described above is operated in the following manner.

As illustrated in FIGS. 3 and 7, the core elevator 41 is positioned at the lowest position restricted by the stopper 403 in a state right before drilling work is started, in which the drill bit 30 does not reach a sea floor 15, and the opening and closing valve body 44 thereof is positioned at a position where the connecting part 451 thereof is opposite to and comes into contact with the tapered part 412 of the core elevator body 43, i.e., at the lowest position to the core elevator body 43 by its own weight and the weight of the flow-able coating material 47 filled into the flow-able coating material reservoir 50.

In this state, the flow-able coating material-ejecting openings 532 are linked with the linking holes 431, but valve openings at the other ends of the linking holes 431 are closed by the valve body part 45, whereby the space within the central through-hole in the core elevator body 43 is shut off from the flow-able coating material-ejecting openings 532. Accordingly, the flow-able coating material 47 does not flow out in this state.

When the drilling of the crust 16 is then started as illustrated in FIGS. 4 and 8, the outer barrel 23 is rotated and goes down from the sea floor 15 while drilling so as to form an annular drilled groove. The opening and closing valve body 44 in the core elevator 41 is pushed up by contact of the working disk 46 with the sea floor 15 relatively upward to a position where the flange 442 comes into contact with the projected contact parts 433.

At this time, the core elevator body 43 of the core elevator 41 is not moved relatively to the inner barrel 40, but the connecting part 451 of the opening and closing valve body 44 is separated upward from the tapered part 412, and so the space within the central through-hole in the core elevator 41 is linked with the flow-able coating material-running channel 53 through the linking channel 432.

As a result, a state that the core elevator 41 is allowed to lift in the flow-able coating material reservoir 50 is achieved. The reason for it is that the flow-able coating material 47 in the flow-able coating material reservoir 50 can be caused to flow out through the flow-able coating material-running channel 53, linking holes 431 and linking channel 432.

On the other hand, the flow-able coating material 47 flown out from the central through-hole in the core elevator 41 comes to reach a peripheral region of the upper surface of the working disk 46 and the surface of a columnar core sample portion 371 formed halfway through the opening 404 for inserting the columnar crustal core portion as illustrated in FIG. 8.

In this state, a vertically movable distance of the opening and closing valve body 44 in the core elevator 41 is a separation distance between the flange 442 of the opening and closing valve body 44 and the projected contact parts 433 of the core elevator body 43 in the state that the opening and closing valve body 44 is positioned at the lowest position where the connecting part 451 of the opening and closing valve body 44 is opposite to and comes into contact with the tapered part 412 to be supported as illustrated in FIG. 6. However, this movable distance is controlled to a distance shorter than the height of the upper space part 411.

In a state that the opening and closing valve body 44 is positioned at the highest position, namely, as illustrated in FIG. 8 or 9, a state that it is raised relatively to the core elevator body 43, and the flange 442 comes into contact with the projected contact parts 433, the O-ring 452 of the opening and closing valve body 44 does thereby not deviate from the upper space part 411 though positioned above the linking holes 431, so that a liquid-tight state between the core elevator body 43 and the flow-able coating material reservoir 50 is retained.

If the movable distance of the opening and closing valve body 44 is greater than the height of the upper space part 411, the connecting part 451 is exposed to the flow-able coating material reservoir 50 when the opening and closing valve body 44 is positioned at its highest position, so that the liquid-tightness in the core elevator 41 cannot be achieved.

When the drilling step is further progressed as illustrated in FIGS. 5 and 9, the outer barrel 23 and inner barrel 40 go down with the drilling, but the core elevator 41 is relatively lifted in the internal space of the inner barrel body 401 by the opening and closing valve body 44 positioned at the highest position and relatively pushed up by the surface of the columnar core sample portion 371. Thereby, in the internal space of the inner barrel body 401, are formed a flow-able coating material reservoir 50, whose lower end is gradually rising, over the lifting core elevator 41 and a crustal core sample-receiving space 51, whose upper end is gradually rising, under the core elevator 41. The columnar crustal core portion 371 formed by the drilling gradually enters the crustal core sample-receiving space 51 and is received therein.

On the other hand, when the core elevator 41 is lifted relatively to the inner barrel body 401, and the whole core elevator body 43 passes through a position where the flow-able coating material-ejecting openings 532 are formed and is positioned above the position, the flow-able coating material reservoir 50 is held in a state linked with the crustal core sample-receiving space 51 through the flow-able coating material-running channel 53 and flow-able coating material-ejecting openings 532.

Pressure is applied to the flow-able coating material 47 kept in the flow-able coating material reservoir 50 by lifting the core elevator 41. As a result, the flow-able coating material 47 is ejected inwardly in a radial direction of the crustal core sample-reserving space 51 with adequate power from the ejecting openings 532 through the flow-able coating material-running channel 53.

At this time, the outer peripheral surface of the columnar crustal core portion 371 formed by rotation of the cutter elements 31 of the drill bit 30 is in a state positioned slightly inside the inner periphery of the crustal core sample-receiving space 51, so that a narrow annular gap G is defined between the outer peripheral surface of the columnar crustal core portion 371 and the inner peripheral wall surface of the crustal core sample-receiving space 51. In other words, the columnar crustal core portion 371 is in a state received in the crustal core sample-receiving space 51 through the annular gap G.

When the columnar crustal core portion 371 gradually enters the crustal core sample-receiving space 51, the flow-able coating material 47 is forcedly ejected on the whole outer peripheral surface thereof when the core portion passes through the flow-able coating material-ejecting openings 532.

More specifically, the columnar crustal core portion 371 formed by drilling the surrounding thereof enters the crustal core sample-receiving space 51 through the central opening in the drill bit 30 and the opening 404 for inserting the columnar crustal core portion relatively to downward movement of the outer barrel 23 and inner barrel 40 with the progress of the drilling. At this time, the flow-able coating material 47 ejected inwardly in the radial direction from the flow-able coating material-ejecting openings 532 is sprayed on and caused to adhere to the outer peripheral surface of the columnar crustal core portion 371. As a result, the whole outer peripheral surface of the columnar crustal core portion 371 is coated with the flow-able coating material 47.

As described above, the columnar crustal core portion 371 entered into the crustal core sample-receiving space 51 in a state coated with the flow-able coating material 47 is cut out at a lower portion thereof and taken. This crustal core portion is recovered as a crustal core sample together with the inner barrel 40 on the drill ship 10 (see FIG. 1) through the interior of the drill pipe 21 (see FIGS. 1 and 2) by a wire or the like.

Figure 10:
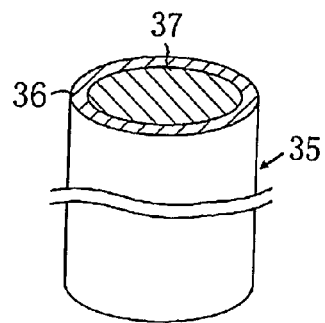
FIG. 10 is a sectional view illustrating a crustal core sample coated with a flow-able coating material, taken perpendicularly to the axis of a barrel.
Figure 11:
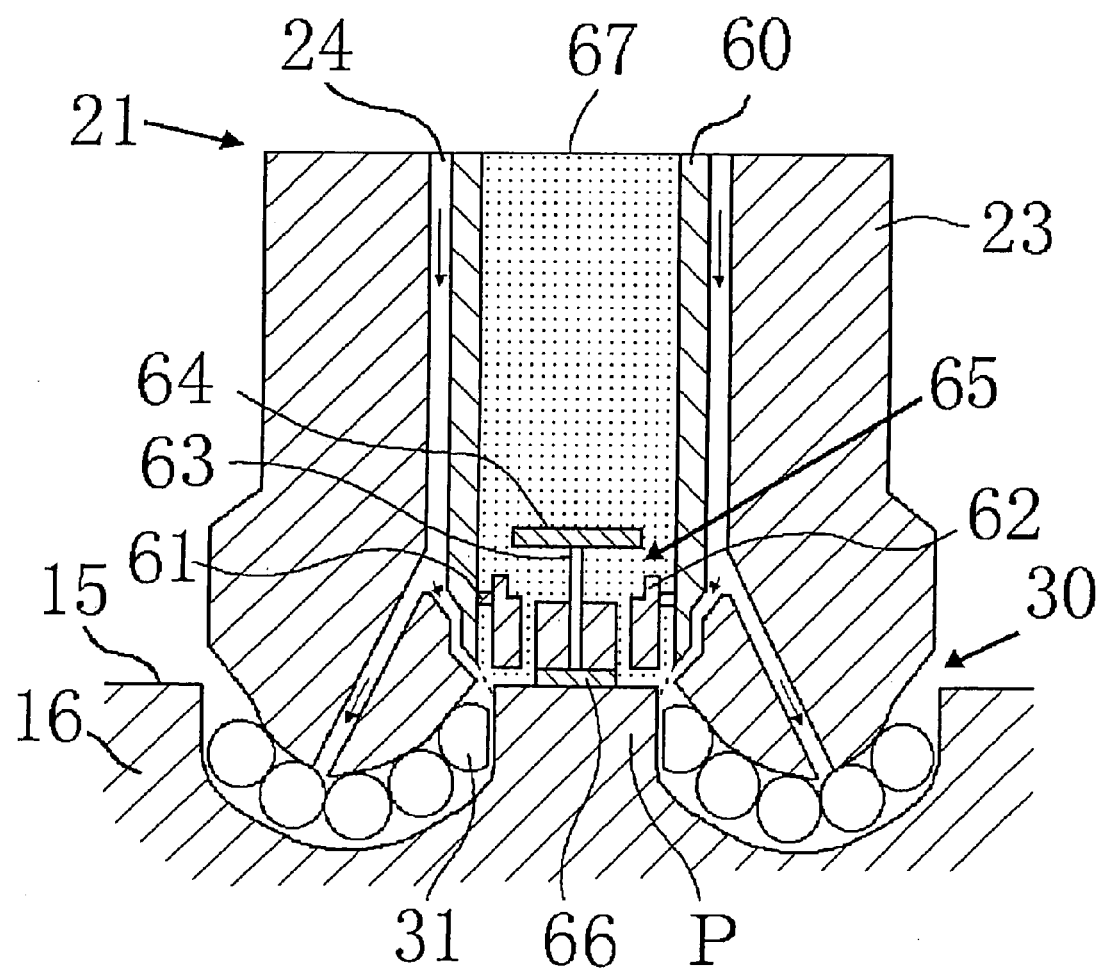
FIG. 11 is a sectional view illustrating a drill pipe and a drill bit in a conventional crustal core sampler right after submarine drilling is started, with a section taken along an axis of a pipe partly schematically shown.
Figure 12:
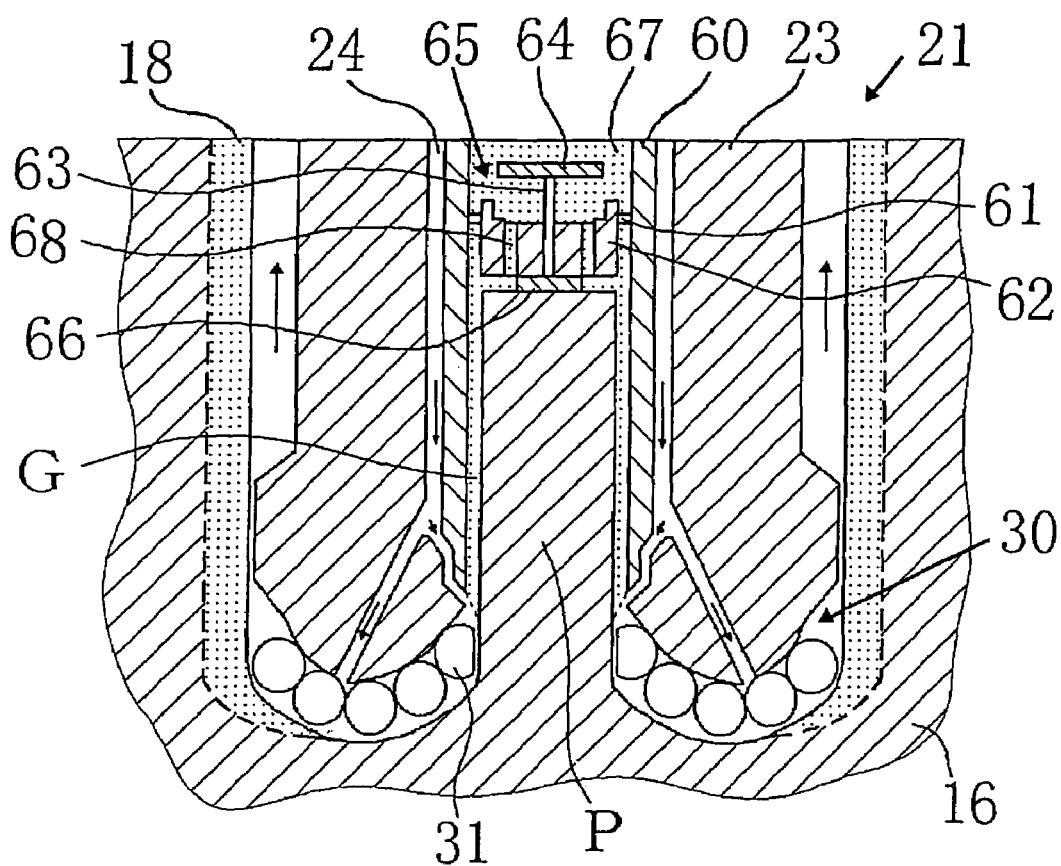
FIG. 12 is a sectional view illustrating the drill pipe and the drill bit in the conventional crustal core sampler during the submarine drilling, with a section taken along the axis of the pipe partly schematically shown.

Since the flow-able coating material 47 has fluidity, it comes around to an end surface formed at the time the columnar crustal core portion 371 has been cut out. As a result, the outer surface of the resulting crustal core sample 35 comes to be completely coated with the flow-able coating material 47. In such a manner, a crustal core sample 35 in a state that a flow-able coating material layer 36 has been formed on the outer surface of a crustal core 37 as illustrated in FIG. 10 is formed.

In the above crustal core sampler, the amount of the flow-able coating material fed through the flow-able coating material-running channel 53 may be suitably selected according to various factors such as the kind or condition of geology in the crust to be drilled, research objects on the crustal core sample taken, physical properties of the flow-able coating material and drilling speed.

The feeding rate of the flow-able coating material is suitably selected in view of various constructional conditions on the crustal core sampler, for example, an area of a section perpendicular to the running direction of the flow-able coating material in the flow-able coating material-running channel 53, an inner diameter of the flow-able coating material reservoir, the total opening area of the inlet openings 531 or ejecting openings 532, and the like, and various operational conditions of the crustal core sampler, for example, physical properties of the flow-able coating material, drilling speed and the like.

The amount of the flow-able coating material ejected is set within a proper range, whereby the crustal core sample can be obtained in a state that its surface has been surely coated with the flow-able coating material.

The ejection speed of the flow-able coating material ejected from the flow-able coating material-running channel to the crustal core sample-receiving space may be suitably selected according to various factors such as the kind or condition of geology in the crust to be drilled, research objects on the crustal core sample taken, physical properties of the working fluid and drilling speed. This ejection speed of the flow-able coating material can be achieved by suitably setting the total opening area and opening form of the ejecting openings 532 and the number of the ejecting openings 532, etc. according to the feeding rate of the flow-able coating material.

The flow-able coating material is ejected from the flow-able coating material-ejecting openings 532 at a proper speed, whereby contaminants adhered to the outer peripheral surface of the columnar crustal core portion 371 can be washed off with high efficiency.

In the above crustal core sampler, various materials have been known as the working fluid, however, those composed by adding for example, weighting agent such as barite, polymer substances, dispersing deflocculants, surfactants, lost circulation materials, borehole wall stability reinforcing agents and the like, to aqueous dispersion having, for example, clays exhibiting anionic property such as bentonite as its main component in a suitable proportion as needed are used.

According to the crustal core sampler having the structure that the flow-able coating material-running channel is provided in a state independent of the internal space of the inner barrel body, it is advantageous in a view that since the flow-able coating material is directly fed to the columnar crustal core portion from the flow-able coating material-ejecting mechanism, the flow-able coating material is applied to the columnar crustal core portion without being mixed and diluted with the working fluid.

As described above, the method of coring a crustal core sample using the flow-able coating material by the crustal core sampler having the working fluid supplying mechanism is basically preferable, however, in this method, there is a problem of a contamination of the crustal core sample by the contaminants from the working fluid, as described above.

The present invention is that uses a flow-able material composed of a colloidal particles capturing polymer substance and a water-absorbing polymer substance as a coating material in the method of coring a crustal core sample for coring the crustal core sample in a state coated by the flow-able coating material.

According to the present invention, a crustal core sample can be cored in a state surely and sufficiently prevented from a contamination by the working fluid by the function of the component of the flow-able coating material even in a coring method of a crustal core sample in which the working fluid is used.

According to the present invention, in a method of coring a crustal core sample using a flow-able coating material, a flow-able coating material composed of a colloidal particles capturing polymer substance and a water-absorbing polymer substance is used. In the method, the flow-able coating material can be used in a state either each of the colloidal particles capturing polymer substance and the water-absorbing polymer substance are not mixed or mixed.

The colloidal particles capturing polymer substance is the polymer substance having a colloidal particles capturing ability by aggregating function. The term "colloidal particles capturing ability by aggregating function" means a function of aggregating colloidal particles stably dispersed in, for example, water, which is a dispersing medium by achieving a state that an electrical charge balance exists between the water and the colloidal particles becomes unbalanced, to form, for example, aggregated mass formed of the colloidal particles themselves, or aggregated mass formed with a part of the polymer substance as a core, thereby, at the same time, incorporating and fixing the aggregated mass through, for example, ionic bonds.

As specific examples of the colloidal particles capturing polymer substance forming the flow-able coating material, is preferably mentioned at least one selected from, for example, copolymer of acrylamide with quaternary ammonium salt compound, copolymer of acrylamide with phosphonium salt compound, cationic denatured product of polyacrylamide, cationic vinyllactam-acrylamide copolymer, cyclized polymer of diallylammonium halide, polyvinylpyridine, quaternary ammonium salt obtained by functioning diamine to copolymer of isobutylene and maleic anhydride, polymer of vinylimidazoline, polymer of dialkylaminoethyl(meta)acrylate, polyethyleneimine, polycondensation product of alkylenedichloride and alkylenepolyamine, polycondensation product of aniline and formalin, polycondensation product of alkylenediamine and epichlorohydrin, polycondensation product of ammonium and epichlorohydrin, polycondensation product of aspartic acid and hexamethylenediamine, cationic denatured product of pitch, cationic polymer substance such as chitosan, sodium polyacrylate, galactomannan, sodium alginic acid, starch, carboxymethyl cellulose-sodium salt, gelatin, nitrocellulose, methylcellulose, hydroxypropylmethylcellulose, pectic acid, pectinic acid, carrageenin, proteoglycan, glycoprotein, gellan gum and xanthan gum.

As the colloidal particles capturing polymer substance, or used cationic polymer substance, anionic polymer substance or nonionic polymer substance in accordance with, for example, the nature of the circulating fluid in order to achieve the suitable colloidal particles capturing ability to be exhibited.

In the present invention, the colloidal particles capturing polymer substance is preferably a cationic polymer substance because microscopic particles contained in the working fluid are usually in anionic state of negative charge.

In the above-described specific examples of the colloidal particles capturing polymer substance, can be mentioned copolymer of acrylamide and quaternary ammonium salt compound and copolymer of acrylamide with phosphonium salt compound as the preferable cationic polymer substance.

The colloidal particles capturing polymer substance having specific ionic property can be obtained by copolymerizing, a monomer having a polymerizable functional group of an unsaturated double bond in its molecule, singly or with other copolymerizable monomer, or by reacting a monomer composition which forms a polymer by reaction.

As specific examples of such monomer, can be mentioned nonionic monomer such as, for example, diallyldimethylammonium salt a counter ion of which is a chloride or bromide ion, acrylamide, vinyllactam, diallylamine, vinylpyridine, isobutylene, maleic anhydride, stylene, vinylimidazoline, dialkylaminoethylacrylate, ethyleneimine, alkylenedichloride, alkyleneamine, aniline, formaldehyde, alkylenediamine, epichlorohydrin, aspartic acid, hexamethylenediamine, sodium vinylsulfonate and the like.

The water-absorbing polymer substance making up the flow-able coating material with the above described colloidal particles capturing polymer substance has, for example, a hydrophilic group in its chemical structure, and has a function of fixing water by absorbing water by itself to be swelled.

As the water-absorbing polymer, can be used polymer or copolymer with proper monomer. As specific example of such monomer, can be mentioned acrylamide, methacrylamide, N,N-dimethylacrylamide, N-methyl-acrylamide, N-methylmethacrylamide, N-vinyl-N-methyl-acetamide, N-isopropylacrylamide, N-(2-hydroxypropyl)-acrylamide, N-(2-hydroxypropyl)methacrylamide, N,N-dimethyl methacrylate, 2-hydroxyethyl acrylate, 2-hydroxyethyl methacrylate, hydroxypropyl methacrylate, 4-hydroxybutyl methacrylate, N-acryloyltris(hydroxy-methyl)methylamine, N-methacryloyltris(hydroxymethyl)-methylamine, vinylpyrrolidone and N-acryloylmorpholine and the like.

The either one or both of the colloidal particles capturing polymer substance and the water-absorbing polymer substance forming the flow-able coating material are preferably the polymer substances having an antimicrobial property and, in this case, the resulting flow-able coating material becomes the one having the antimicrobial property. According to the flow-able coating material having the antimicrobial property, activities and increase of microorganisms adhered on to the crustal core sample in advance can be controlled and prevented, and at the same time, the penetration of the microorganisms from outside is prevented, thereby preventing the crustal core sample from contaminations caused by these factors.

To obtain the polymer substances having the antimicrobial property, a compound having an atomic group of antibacterial property can be used as a monomer component for obtaining a polymer making up the polymer substance. As such antimicrobial monomer, can be mentioned, for example, quaternary ammonium salt compound having unsaturated double bond and phosphonium salt compound having unsaturated double bond.

As such antimicrobial monomer compound, specifically, one or more compounds selected from among an aromatic quaternary ammonium salt compound represented by the following general formula (1), an acryloyloxyalkyltrialkylammonium salt compound and a methacryloyloxyalkyltrialkylammonium salt compound represented by the following general formula (3), and an aromatic phosphonium salt compound represented by the following general formula (2) may preferably be used.

Chemical Formula 1

General formula (1):

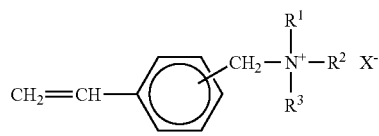

wherein $R^1$ means a linear or branched alkyl group having 1 to 18 carbon atoms, $R^2$ and $R^3$ are methyl groups, and $X^-$ denotes a halogen ion.

Chemical Formula 2

General formula (2):

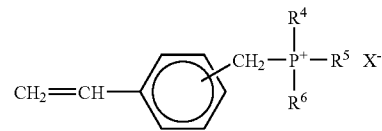

wherein $R^4$, $R^5$ and $R^6$ independently mean a linear or branched alkyl group having 1 to 18 carbon atoms, and $X^-$ denotes a halogen ion, with the proviso that $R^4$, $R^5$ and $R^6$ may be the same or different from one another.

Chemical Formula 3

General formula (3):

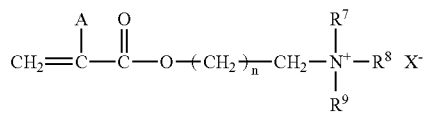

wherein $R^7$, $R^8$ and $R^9$ may be the same or different from one another and independently mean a linear or branched alkyl group having 1 to 16 carbon atoms, $X^-$ denotes a halogen ion, and A represents a hydrogen atom or methyl group.

As specific preferable examples of the antimicrobial monomer compounds, may be mentioned vinylbenzyl dimethyl-n-octylammonium salts, vinylbenzyldimethyl-n-decylammonium salts, vinylbenzyldimethyl-n-dodecylammonium salts and vinylbenzyldimethyl-n-hexadecylammonium salts for examples of the antimicrobial monomers represented by the general formula (1).

As examples of the antimicrobial monomer compounds represented by the general formula (2), may be mentioned vinylbenzyltri-n-butylphosphonium salts, vinylbenzyltri-n-octylphosphonium salts, vinylbenzyltri-n-decyl-phosphonium salts and vinylbenzyltri-n-dodecylphosphonium salts and the like.

As examples of the antimicrobial monomer compounds represented by the general formula (3), may be mentioned 2-acryloyloxyethyltrimethylammonium salts and 2-methacryloyloxyethyltrimethylammonium salts and the like.

As examples of other antimicrobial monomer compounds, may be mentioned acrylamidopropyltrimethylammonium salts, methacrylamidopropyltrimethylammonium salts, acryloyloxyalkylpyridinium salt compounds and methacryloyloxyalkylpyridinium salt compounds and the like.

In the above-described respective compounds, a counter ion is preferably a chloride or bromide ion.

When the antimicrobial monomer is used, the antimicrobial monomer component is preferably used in a proportion of 1 to 10 mol %, particularly 3 to 8 mol % of the total monomer.

Polymers making up the colloidal particles capturing polymer substance and the water-absorbing polymer substance may also be those obtained from a composition having a crosslinkable monomer. As the crosslinkable monomer, can be mentioned one or more of, for example, N,N'-methylenebisacrylamide, diethylene glycol diacrylate, diethylene glycol dimethacrylate, diethylene glycol divinyl ether, ethylene glycol dimethacrylate, poly(ethylene glycol)

diacrylate, poly(ethylene glycol) dimethacrylate and poly (propylene glycol) dimethacrylate and the like.

No particular limitation is imposed on the process for obtaining the colloidal particles capturing polymer substance or the water-absorbing polymer substance, and a (co)polymerization process generally used, specifically, a radical (co)polymerization reaction using a radical polymerization initiator may be preferably utilized.

As the radical polymerization initiator, any radical polymerization initiator may be used without particular limitation so far as it is generally used. As examples thereof, may be mentioned hydrogen peroxide, ammonium persulfate, potassium persulfate, t-butyl hydroperoxide, azobisisobutyronitrile, 2,2'-azobis(2-methylpropionamide)dihydrochloride, 2,2'-azobis[2-(2-imidazolin-2-yl)propane] dihydrochloride and 2,2'-azobis(2-amidinopropane)dihydrochloride and the like. In addition, publicly known redox initiators, for example, hydrogen peroxide and ferrous sulfate, and potassium persulfate and sodium hydrogensulfite may also be used.

As a solvent used in the polymerization reaction, may be used water, a mixed solvent of water and a water-soluble organic solvent, etc. As specific examples of the water-soluble organic solvent, may be mentioned alcohols such as methanol, ethanol, isopropanol and n-propanol, amide compounds such as formamide and dimethylformamide, and polar solvents such as dioxane, acetonitrile and dimethyl sulfoxide and the like.

The polymerization reaction is only required to be conducted at a temperature and for a period of time according to the kinds of the monomer(s) and radical polymerization initiator used and other conditions. For example, the polymerization reaction is conducted at a temperature of 50 to 90° C. for about 3 to 24 hours. In this polymerization reaction, it is necessary to conduct the reaction under an inert gas atmosphere with, for example, nitrogen gas.

In the present invention, those composed of the above-described colloidal particles capturing polymer substance and the water-absorbing polymer substance are used as the flow-able coating material, therefore, the crustal core sample is cored in a state coated with the flow-able coating material.

Even when the contaminants from the working fluid are adhered on to the outer surface of the cored crustal core sample by the contact of the working fluid, in advance to the flow-able coating material, the colloidal particles in the working fluid which are adhered on to the outer surface of the crustal core sample are captured by the aggregating function of the colloidal particles capturing polymer substance in the coating material layer contacted thereto, and at the same time, water in the working fluid adhered on to the outer surface of the crustal core sample is absorbed and fixed by the water-absorbing polymer substance contacted thereto, because the coating material according to the present invention comprising a colloidal particles capturing ability by aggregating function and a water-absorbing polymer substance. As a result, the contaminants from the working fluid, namely, the microorganisms and the other contaminants introduced on the outer surface of the crustal core sample along with the colloidal particles and water of the working fluid are fixed at the coating material layer and a transfer thereof is inhibited, thereby the crustal core sample can be cored in a state sufficiently and surely prevented from contamination by the contaminants.

When the flow-able coating material has the antimicrobial property, an ecosystem of the crustal core sample is sufficiently protected from outside, and moreover, the microorganisms do not increase in the coating material layer itself, therefore the coating material layer does not become a source of contamination of the microorganisms to the crustal core sample.

No particular limitation is imposed on the method of drilling of the crust related to the present invention, and it can be conducted with publicly known various drilling methods. In particular, the method can be easily practiced in the drilling of the submarine crust making good use of a drill ship such as the above-described riser drilling method. However, methods are not limited to the riser drilling method.

Although the method of coring a crustal core sample according to the present invention have been described specifically above, various modifications may be added to the present invention.

For example, the flow-able coating material is not required to be ejected from the flow-able coating material ejecting openings perpendicularly to an axial direction, and it may be ejected in a direction inclined downward.

PREPARATION EXAMPLE (Preparation of Nonionic Colloidal Particles Capturing Polymer Substance)

A pressure-proof bottle, which was a reaction vessel, was charged with 4.9.7 g (700 mmol/L) of acrylamide and 0.028 g (1.0 mmol/L) of 2,2'-azobis(2-amidinopropane)dihydrochloride, and pure water which was a polymerization reaction solvent to obtain 100 ml of polymerization reaction solution, and internal air in the pressure-proof bottle was substituted with nitrogen gas for 30 minutes. Then, the pressure-proof bottle holding the polymerization reaction solution was placed in an incubator of temperature of 70° C. to conduct a polymerization reaction treatment.

Resulting polymer was taken out from the pressure-proof bottle and washed by using ethanol and ion exchanged water to remove the unreacted residual monomer and dried, whereby obtaining Colloidal particles capturing polymer substance Al in a state of powder. Colloidal particles capturing polymer substance Al thus obtained exhibited weak cationic property in the strict sense.

(Preparation of Cationic Colloidal Particles Capturing Polymer Substance)

In a 5 L beaker, 60 g of processed product of polymeric chitosan (product name; Flownak #250, manufactured by Kyowa Technos Co., Ltd.) was dissolved in 3 L of water, whereby obtaining Colloidal particles capturing polymer substance A2 composed of an aqueous solution of polymeric chitosan in a gel state.

(Preparation of Anionic Colloidal Particles Capturing Polymer Substance)

In a 5 L beaker, 30 g of sodium polyacrylate (manufactured by Wako Pure Chemical Industries, Ltd.) having polymerization degree of 22,000 to 70,000 was dissolved in 3 L of water, whereby obtaining Colloidal particles capturing polymer substance A3 composed of an aqueous solution of sodium polyacrylate in a gel state.

(Preparation of Water-Absorbing Polymer Substance)

A pressure-proof bottle, which was a reaction vessel, was charged with 23.6 g (665 mmol/L) of acrylamide, 0.325 g (4 mmol/L) of N,N'-methylenebisacrylamide, 0.24 g (1.7 mmol/L) of 2,2'-azobis(2-amidinopropane) dihydrochloride and 3.4 g (35 mmol/L) of 2-acryloyloxyethyltrimethylammoniumchloride, and pure water which was a polymerization reaction solvent to obtain 500 ml of polymerization reaction solution, and internal air in the pressure-proof bottle was substituted with nitrogen gas for 30 minutes. Then, the pressure-proof bottle holding the polymerization reaction solution was placed in a incubator of temperature of 70° C. to conduct a polymerization reaction treatment.

Resulting polymer was taken out from the pressure-proof bottle and washed by using ethanol and ion exchanged water to remove the unreacted residual monomer and dried and grinded by using ball mill, whereby obtaining Water-absorbing polymer substance B1 in a state of powder having an antimicrobial property.

EXAMPLE 1

Nonionic Colloidal particles capturing polymer substance A1 and Water-absorbing polymer substance B1 obtained as above-described process were mixed in a proportion of 1:20 in terms of ratio of dry weight, and water was added to the resultant mixture, to obtain Flow-able coating material 1 having a viscosity of 5000 mPa·sec.

Using the crustal core sampler having the construction shown in FIG. 3, using the above-described Flow-able coating material 1 as a flow-able coating material, and supplying a fluorescent beads containing working fluid having a viscosity of 50 mPa·sec and specific gravity of 1.03 in a condition that the rate of supply was 100 L/min, Oya stone (rhyolitic breccia tuff) as the object of drilling was drilled at a condition of: load against the drill bit of 1200 kg, revolving speed of the drill bit of 25 rpm and transporting rate of the working fluid of 100 L/min whereby obtaining mock crustal core sample of about 50 cm long.

The working fluid contained fluorescent beads (Fluoresbrite Yellow Green microspheres: manufactured by PolySciences Inc.) having a diameter of 0.2 μm in a proportion of $1.0 \times 10^7$ pieces/ml.

A condition of the resultant mock crustal core sample was evaluated visually.

The flow-able coating material coating the outer surface of the resultant mock crustal core sample was removed, and from a belt-like region having central width of 10 cm in a longitudinal direction, constitutional substances of the surface layer portion of 1 mm thick over the whole periphery surface were taken as samples. Number of the fluorescent beads contained in the each sample was counted by a method described subsequently. The results are shown in the table 1.

(Method of Counting Number of Fluorescent Beads)

A 50 ml centrifuge tube was charged with 1 g of the sample together with 30 ml of aqueous solution of sodium chloride, a concentration of which was 30 mass %, to obtain a sample mixture solution, and the sample mixture solution was fully stirred by vortex while smashing lumps of particles having a diameter of more than about 2 mm by suitable means, and left at dark place of the room temperature for 48 hours. The supernatant liquid of the sample mixture solution was skimmed and filtered with the filter having a pore size of 0.1 μm, and fluorescent beads remained on the filter were washed and the number thereof was counted by using a fluorescence microscope.

EXAMPLE 2

Flow-able coating material 2 was prepared as the same manner as in the example 1 except that Colloidal particles capturing polymer substance A2 was used instead of Colloidal particles capturing polymer substance A1 in the example 1, and mock crustal core sample was obtained as the same manner as in the example 1 by using Flow-able coating material 2, and evaluation was conducted. The results are shown in the table 1.

EXAMPLE 3

Flow-able coating material 3 was prepared as the same manner as in the example 1 except that Colloidal particles capturing polymer substance A3 was used instead of Colloidal particles capturing polymer substance A1 in the example 1, and mock crustal core sample was obtained as the same manner as in the example 1 by using Flow-able coating material 3, and evaluation was conducted. The results are shown in the table 1.

CONTRASTIVE EXAMPLE 1

A mock crustal core sample was obtained as the same manner as in the example 1 except that Flow-able coating material 1 was not supplied. The condition of the mock crustal core sample was evaluated visually, and the number of the fluorescent beads was counted. The results are shown in the table 1.

COMPARATIVE EXAMPLE 1

A flow-able substance having viscosity of about 5000 mPa·sec was prepared by adding water to Nonionic Colloidal particles capturing polymer substance A1. A mock crustal core sample was obtained as the same manner as in the example 1 except that the flow-able substance was used as a comparative flow-able coating material. The condition of the crustal core sample was evaluated visually, and the number of the fluorescent beads was counted as the same manner as in the example 1. The results are shown in the table 1.

COMPARATIVE EXAMPLE 2

A flow-able substance having viscosity of about 5000 mPa·sec was prepared by adding water to Water-absorbing polymer substance B1. A mock crustal core sample was obtained as the same manner as in the example 1 except that the flow-able substance was used as a comparative flow-able coating material. The condition of the crustal core sample was evaluated visually, and the number of the fluorescent beads was counted as the same manner as in the example 1. The results are shown in the table 1.

TABLE 1

| | Flow-able coating material | | |
|---|---|---|---|
| Example | Colloidal particles capturing polymer substance | Water-absorbing polymer substance | Number of fluorescent beads (count) |
| Example 1 | A1 | B1 | $2.0 \times 10^2$ |
| Example 2 | A2 | B1 | 70 |
| Example 3 | A3 | B1 | $5.0 \times 10^2$ |
| Contrastive Example 1 | — | — | $5.0 \times 10^4$ |
| Comparative Example 1 | A1 | — | $1.0 \times 10^4$ |
| Comparative Example 2 | — | B1 | $2.0 \times 10^4$ |

From the results shown in the above table 1, when the flow-able coating material is composed of the colloidal particles capturing polymer substance and the water absorbing polymer substance, it is clear that adhesion of the contaminants is little since the number of the fluorescent beads entering into the surface layer portion of the mock crustal core sample was little. Especially, when Cationic Colloidal particles capturing polymer substance A2 was used as the colloidal particles capturing polymer substance, the number of the fluorescent beads entering into the surface layer portion of the mock crustal core sample was significantly little, it is therefore clear that adhesion of the contaminants is significantly little.

On the other hand, in the Contrastive example 1, in which the flow-able coating material was not used, the number of the fluorescent beads was significantly large. Therefore, it is understood that the adhesion of the contaminants would be remarkably high.

According to the Comparative example 1, in which only the colloidal particles capturing polymer substance was used as the flow-able coating material, the number of the fluorescent beads was remarkably decreased compare to Contrastive example 1. Therefore, the effect of the colloidal particles capturing polymer substance was recognized, however, still great number of the fluorescent beads was counted. It is considered to be attributable to the fact that the fluorescent beads were transported along with water and adhered to the crustal core sample since the water-absorbing polymer substance was not used in the Comparative example 1.

Further more, according to the Comparative example 2, in which only the water-absorbing polymer substance was used as the flow-able coating material, the number of the fluorescent beads was considerably decreased compare to the Contrastive example 1, but larger than Comparative example 1. Therefore, some effects of the water-absorbing polymer substance was recognized, however, still great number of the fluorescent beads were counted. It is considered to be attributable to the fact that the fluorescent beads were not captured and adhered to the crustal core sample since the Colloidal particles capturing polymer substance was not used.

It is apparent from the above explanation, that by using both of the Colloidal particles capturing polymer substance and the water-absorbing polymer substance, the crustal core sample can be cored in a sufficiently and surely controlled state from the contamination, however, it is difficult to core the crustal core sample in a sufficiently and surely controlled state from the contamination when only one of them was used.

What is claimed is:

1. A method of coring a crustal core sample which comprises using a crustal core sampler equipped with a flowable coating material-ejecting mechanism for ejecting a flowable coating material, and
    ejecting the flowable coating material composed of a polymer substance having a colloidal particle capturing ability by an aggregating function and a water-absorbing polymer substance, from the flowable coating material-ejecting mechanism of the crustal core sampler, thereby coring a crustal core sample in a state coated with the flowable coating material,
    wherein at least either one of the polymer substance having a colloidal particle capturing ability by an aggregating function or the water-absorbing polymer substance has an antimicrobial property.

2. The method of coring a crustal core sample according to claim 1, wherein the crustal core sampler is equipped with a drilling mechanism for drilling crust so as to form an annular drilled groove, a supplying mechanism for a fluid for drilling work having an ejection opening for the fluid for drilling work positioned at the lower end of the drilling mechanism, and a cylindrical barrel, which has an opening for inserting a columnar crustal core portion at its lower end and receives a columnar crustal core portion provided as a crustal core sample in the interior thereof, and
    wherein the cylindrical barrel is provided with the flowable coating material-ejecting mechanism for ejecting the flowable coating material inwardly in a radial direction of the cylindrical barrel at a position in close vicinity of its lower end.

3. The method of coring a crustal core sample according to claim 2, wherein the polymer substance having a colloidal particle capturing ability by an aggregating function is selected from the group consisting of a cationic polymer substance, an anionic polymer substance and a nonionic polymer substance.

4. The method of coring a crustal core sample according to claim 1, wherein the crustal core sampler comprises a cylindrical drill ripe equipped at its lower end with a drill bit having an ejection opening for a fluid for drilling work, and an inner barrel arranged in the cylindrical drill pipe, and
    wherein the inner barrel is equipped with a cylindrical inner barrel body, which has an opening for inserting a columnar crustal core portion at its lower end and receives a columnar crustal core portion formed by drilling and provided as a crustal core sample in the internal space thereof, a core elevator is arranged in an internal space of the inner barrel body and is movably in an axial direction thereof, and
    wherein the flowable coating material-ejecting mechanism comprises a channel-forming member for forming a flowable coating material-running channel with an outer peripheral surface of the cylindrical inner barrel body and a flowable coating material-ejecting opening for ejecting the flowable coating material from the flowable coating material running channel inwardly in a radial direction of the cylindrical inner barrel body at a position in close vicinity of the lower end of the cylindrical inner barrel body, and the cylindrical inner barrel body is arranged in such a manner that the opening for inserting the columnar crustal core portion is positioned above the ejection opening of the fluid for drilling work in the drill pipe.

5. The method of coring a crustal core sample according to claim 4, wherein the polymer substance having a colloidal particle capturing ability by an aggregating function is selected from the group consisting of a cationic polymer substance, an anionic polymer substance and a nonionic polymer substance.

6. The method of coring a crustal core sample according to claim 1, wherein the polymer substance having a colloidal particle capturing ability by an aggregating function is selected from the group consisting of a cationic polymer substance, an anionic polymer substance and a nonionic polymer substance.

* * * * *